United States Patent
Adams et al.

(10) Patent No.: US 9,987,474 B2
(45) Date of Patent: Jun. 5, 2018

(54) ANTISEPTIC SWAB

(71) Applicant: iMed Technology, Inc., Dallas, TX (US)

(72) Inventors: Kyle S. Adams, Dallas, TX (US); Gordon E. Atkinson, Black Mountain, NC (US)

(73) Assignee: iMed Technology, Inc., Dallas, TX (US)

( * ) Notice: Subject to any disclaimer, the term of this patent is extended or adjusted under 35 U.S.C. 154(b) by 78 days.

(21) Appl. No.: 15/285,760

(22) Filed: Oct. 5, 2016

(65) Prior Publication Data
US 2018/0093082 A1    Apr. 5, 2018

(51) Int. Cl.
*A61M 35/00* (2006.01)
*A61F 13/40* (2006.01)

(52) U.S. Cl.
CPC ........ *A61M 35/006* (2013.01); *A61M 35/003* (2013.01); *A61M 2210/02* (2013.01)

(58) Field of Classification Search
CPC ........................... A61M 35/00; A61M 35/006
USPC .................................................. 401/132–135
See application file for complete search history.

(56) References Cited

U.S. PATENT DOCUMENTS

| | | | |
|---|---|---|---|
| 3,482,920 A | 12/1969 | Schwartzman | |
| 3,922,099 A * | 11/1975 | Christine | A61M 3/00 222/107 |
| 4,148,318 A | 4/1979 | Meyer | |
| 4,415,288 A * | 11/1983 | Gordon | A61M 35/006 401/132 |
| 4,498,796 A | 2/1985 | Gordon et al. | |
| 4,730,949 A | 3/1988 | Wilson | |
| 4,927,283 A | 5/1990 | Fitjer | |
| 5,042,690 A * | 8/1991 | O'Meara | A61M 35/006 206/15.2 |
| 5,120,301 A | 6/1992 | Wu | |
| 5,769,552 A | 6/1998 | Kelley et al. | |
| 6,536,975 B1 | 3/2003 | Tufts | |
| 7,121,754 B2 | 10/2006 | Bressler et al. | |

(Continued)

OTHER PUBLICATIONS

U.S. Appl. No. 15/878,999 entitled "Antiseptic Swab With Activation Button," filed Jan. 24, 2018 by Kyle S. Adams.

(Continued)

*Primary Examiner* — Jennifer C Chiang
*Assistant Examiner* — Bradley Oliver
(74) *Attorney, Agent, or Firm* — Stevens & Showalter, LLP

(57) ABSTRACT

A liquid dispensing device including an elongated handle having a hollow interior defining a fluid reservoir. A base member is affixed to a lower end of the handle and a frangible cover is secured over a bottom surface of the base member and forms a seal across an opening of the fluid reservoir. A swab head supports an absorbent sponge-like member and includes an upper side supporting a cover-rupturing member. A hinge segment is affixed to the base member and to the swab head, the hinge segment defining a pivot axis about which the swab head pivots to move the swab head from an open position with the cover-rupturing member spaced from the frangible cover to a closed position with the cover-rupturing member extending through the frangible cover and into the opening of the fluid reservoir.

18 Claims, 4 Drawing Sheets

(56) References Cited

U.S. PATENT DOCUMENTS

| | | |
|---|---|---|
| 7,201,525 B2 | 4/2007 | Mohiuddin |
| 8,348,537 B2 | 1/2013 | Cable, Jr. et al. |
| 2002/0076258 A1 | 6/2002 | Crosby et al. |
| 2004/0067090 A1* | 4/2004 | Budds .................. B65D 51/222 401/118 |
| 2004/0162533 A1* | 8/2004 | Alley .................. A61M 35/006 604/290 |
| 2004/0179888 A1 | 9/2004 | Tufts et al. |
| 2006/0039742 A1* | 2/2006 | Cable, Jr. ............ A61M 35/003 401/134 |
| 2007/0231051 A1 | 10/2007 | Flores et al. |
| 2007/0248399 A1 | 10/2007 | Tufts et al. |
| 2008/0058863 A1* | 3/2008 | Quintero .......... A61B 17/00491 606/214 |
| 2010/0168638 A1 | 7/2010 | Korogi et al. |
| 2012/0219347 A1* | 8/2012 | Law .................... A61M 35/006 401/133 |
| 2015/0050065 A1 | 2/2015 | Guzman |
| 2015/0297876 A1* | 10/2015 | Lockwood .......... A61M 35/006 401/134 |
| 2016/0106964 A1* | 4/2016 | Quaglia .............. A61M 35/003 604/310 |
| 2017/0164713 A1* | 6/2017 | Davia ................. A61M 35/006 |
| 2017/0165463 A1* | 6/2017 | Law .................... A61M 35/006 |

OTHER PUBLICATIONS

Design U.S. Appl. No. 29/634,725 entitled "Antiseptic Swab," filed Jan. 24, 2018 by Kyle S. Adams.

\* cited by examiner

ANTISEPTIC SWAB

FIELD OF THE INVENTION

The present application relates generally to liquid dispensers and applicators of the type wherein a premeasured supply of liquid is disposed in an applicator handle for selective dispensing. The device described herein has particular applicability to dispensing of antiseptic solution.

BACKGROUND OF THE INVENTION

Tools for surgical preparations generally may include a sponge which is used by medical personnel to apply an antiseptic solution to a patient's skin. The sponge can be dipped into an antiseptic solution in a container and swabbed onto the patient's skin to prevent live bacteria from entering an incision or wound of the skin. Other devices have been developed that contain an antiseptic solution contained in the device for dispensing the solution from an applicator associated with the device. There is a continuing need for a dispensing device that can be configured for use to dispense a fluid, such as an antiseptic solution, to an applicator swab wherein required manipulation of the device prior to use may be minimized.

SUMMARY OF THE INVENTION

In accordance with one aspect of the invention, a liquid dispensing device is provided comprising an elongated member defining a handle having a hollow interior, the hollow interior defining a fluid reservoir having an opening at a lower end of the elongated member. A base member is affixed to the lower end of the elongated member, the base member having a bottom surface. A frangible cover is secured over the bottom surface and forms a seal across the opening of the fluid reservoir. A swab head defines a lower side supporting an absorbent sponge-like member and an upper side supporting a cover-rupturing member. A hinge segment is affixed to the base member and to the swab head, the hinge segment defining a pivot axis about which the swab head pivots to move the swab head from an open position with the cover-rupturing member spaced from the frangible cover to a closed position with the cover-rupturing member extending through the frangible cover and into the opening of the fluid reservoir.

The bottom surface of the base member and upper side of the swab head may be planar surfaces and may engage each other at a common plane in the closed position of the swab head.

One of the planar surfaces of base member and swab head may include a seal rib extending from the one of the planar surfaces, the seal rib may engage the other of the planar surfaces in the closed position to define a seal surrounding the opening of the fluid reservoir.

The base member and swab head may define respective peripheral edges and a latch tongue may be provided integrally formed with the peripheral edge of one of the base member and the swab head, the latch tongue including pawl means forming a recess thereacross for engaging the peripheral edge on the other of the base member and the swab head to retain the swab head in the closed position.

The hinge segment may be a living hinge formed integrally with the base member and with the swab head.

A through passage may be defined in the swab head aligned with the opening of the fluid reservoir in the closed position.

The cover-rupturing member may be rigidly affixed to the upper side at the through passage.

The cover-rupturing member may include an outer surface defining an angle with an apex at a point located distal from the upper side.

The cover-rupturing member may include a base portion surrounding the through passage in the swab head and the cover rupturing member defines a fluid conduit between the opening of the fluid reservoir and the sponge-like member.

The frangible cover may comprise a thin sheet of material adhered to the bottom surface of the base member.

In accordance with another aspect of the invention, a liquid dispensing device is provided comprising an elongated member defining a handle having a hollow interior, the hollow interior defining a fluid reservoir having an opening at a lower end of the elongated member. A base member is affixed to the lower end of the elongated member, the base member having a bottom surface. A frangible cover comprising a thin sheet of material is adhered to the bottom surface of the base member and forms a seal across the opening of the fluid reservoir. A swab head comprising a plate-like member defines a lower side supporting an absorbent sponge-like member and an upper side with a cover-rupturing member comprising an upward projection rigidly affixed to the upper side. The swab head includes a through passage for passage of fluid from the fluid reservoir to the sponge-like member. A hinge segment is affixed to the base member and to the swab head, the hinge segment defining a pivot axis about which the swab head pivots to move the swab head from an open position with the cover-rupturing member spaced from the frangible cover to a closed position with the cover-rupturing member extending through the frangible cover and into the opening of the fluid reservoir.

In accordance with a further aspect of the invention, a liquid dispensing device is provided comprising an elongated member defining a handle having a hollow interior, the hollow interior defining a fluid reservoir having an opening at a lower end of the elongated member. A base member is affixed to the lower end of the elongated member. The base member has a bottom surface and a peripheral edge defined around the base member. A frangible cover comprising a thin sheet of material is adhered to the bottom surface of the base member and forms a seal across the opening of the fluid reservoir retaining a fluid within the fluid reservoir. A swab head comprising a plate-like member defines a lower side supporting an absorbent sponge-like member and an upper side with a cover-rupturing member comprising an upward projection rigidly affixed to the upper side. The swab head defines a peripheral edge and includes a through passage for passage of fluid from the fluid reservoir to the sponge-like member. A living hinge is formed integrally with the base member and with the swab head, the hinge defining a pivot axis about which the swab head pivots to move the swab head from an open position with the cover-rupturing member spaced from the frangible cover to a closed position with the cover-rupturing member extending through the frangible cover and into the opening of the fluid reservoir. A latch tongue is integrally formed with the peripheral edge of one of the base member and the swab head, the latch tongue including pawl means forming a recess thereacross for engaging the peripheral edge on the other of the base member and the swab head to retain the swab head in the closed position.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
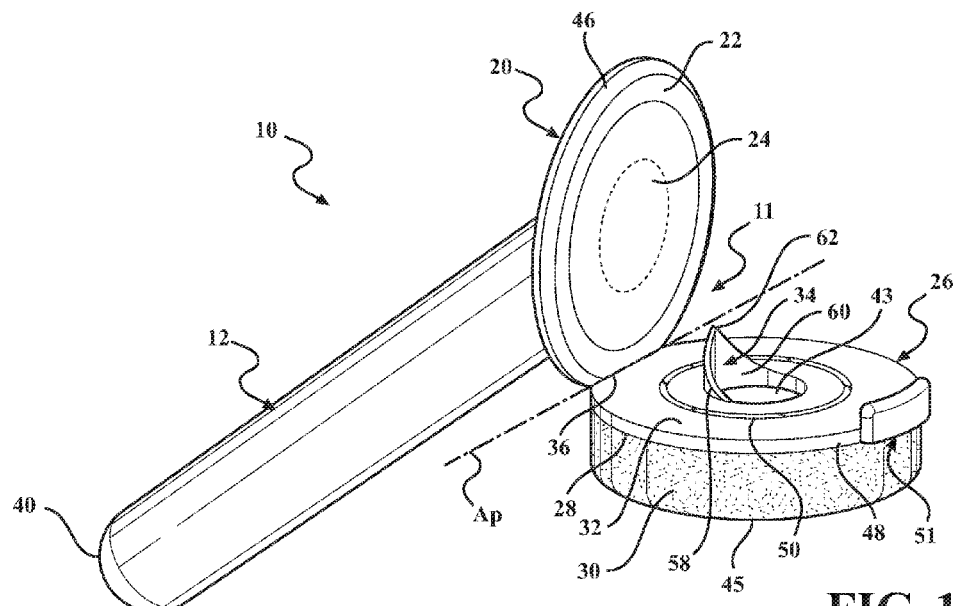
FIG. 1 is a perspective view of a liquid dispensing device and illustrating a swab member in an open position pivoted away from a base member.

Aspects of the invention are illustrated in a first configuration as shown in FIGS. 1-6. Referring initially to FIG. 1, a liquid dispensing device 10 is shown and, in a particular useful configuration, is provided as an antiseptic swab such as may be implemented in medical applications, e.g., as a surgical scrub. The device 10 includes an elongated member defining a handle 12 having a hollow interior. As may be further seen in FIGS. 3 and 4, the hollow interior defines a fluid reservoir 14 having an opening 16 at a lower end 18 of the handle 12.

Figure 2:
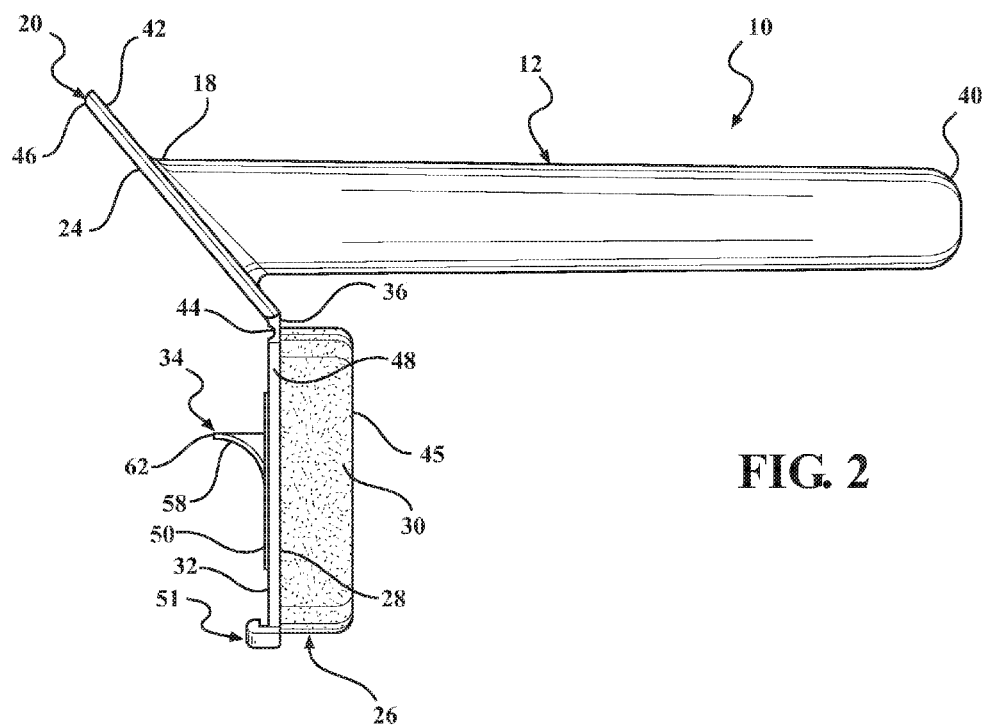
FIG. 2 is an elevation side view of the device of FIG. 1.
Figure 3:
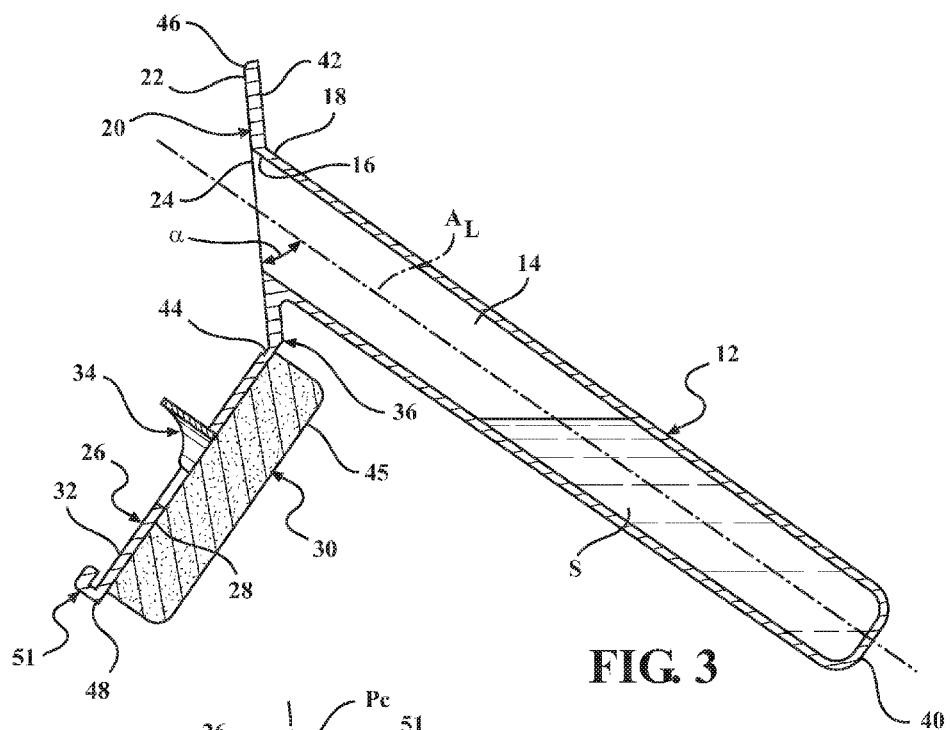
FIG. 3 is a cross-sectional view of the device illustrating the swab member in the open position pivoted away from a base member.
Figure 4:
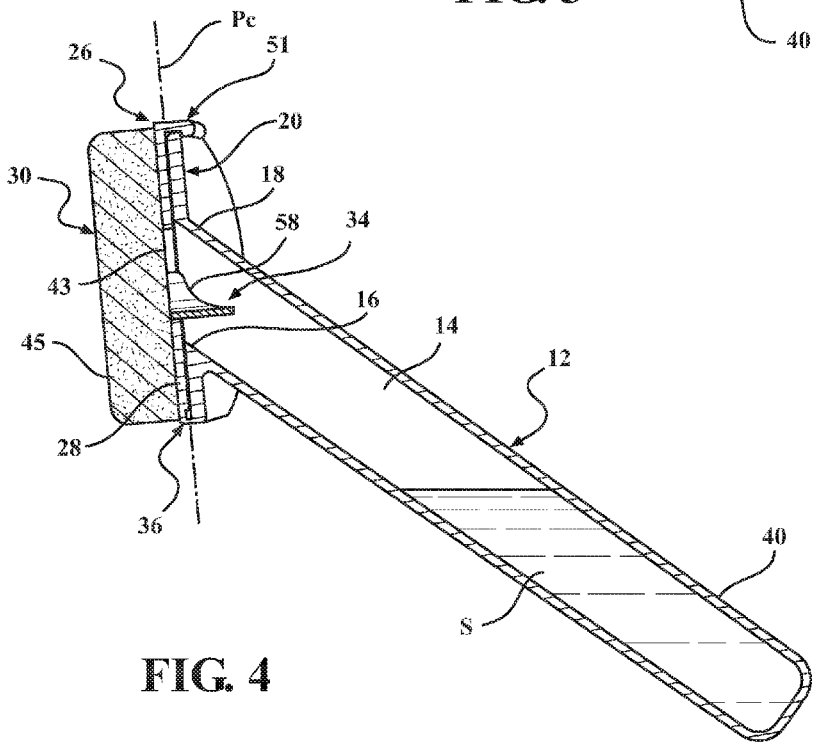
FIG. 4 is a cross-sectional view of the device illustrating the swab member in a closed position pivoted into engagement with the base member.
Figure 5:
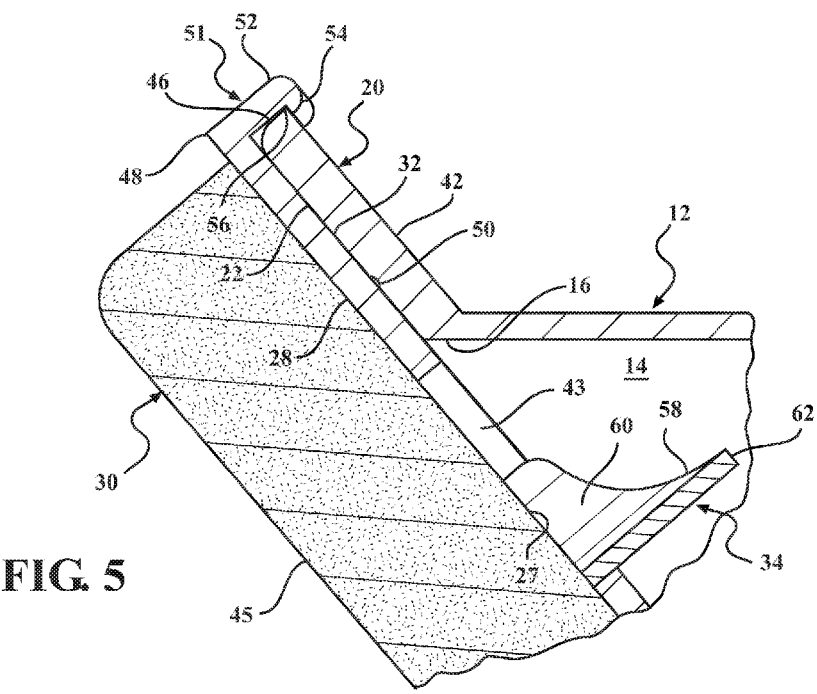
FIG. 5 is an enlarged view of a portion of the device of FIG. 4.
Figure 6:
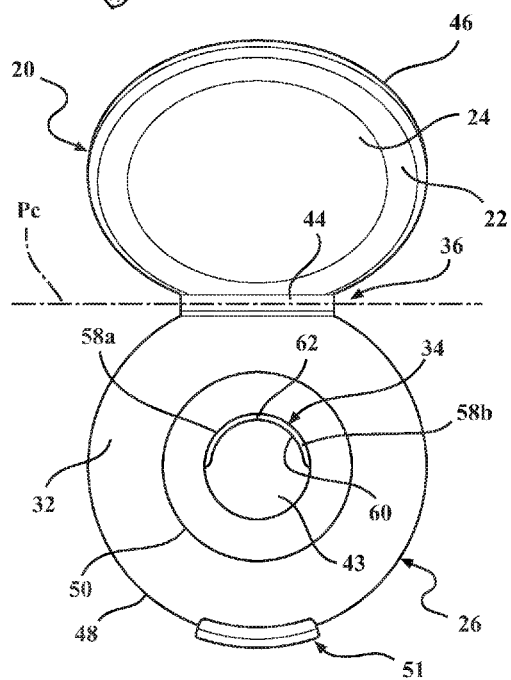
FIG. 6 is a perspective view of the device in the open position and viewing the swab member in plan view.

A base member 20 is affixed to the lower end 18 of the handle 12 and has a bottom surface 22 facing in a direction away from the handle 12. A cover member comprising a frangible cover 24 is adhered or otherwise secured over at least a portion of the bottom surface 22 and forms a fluid tight seal across and surrounding the opening 16 of the fluid reservoir 14. The frangible cover 24 is a part of the base member 20 that is capable of being broken. A swab head 26 is located adjacent to the base member 20 and defines a lower side 28 supporting an absorbent sponge-like member 30 and an upper side 32 supporting a cover-rupturing member 34. A hinge segment 36 is affixed to the base member 20 and to the swab head 26. The hinge segment 36 defines a pivot axis $A_P$ (FIG. 5) about which the swab head 26 pivots to move the swab head 26 from an open position with the cover-rupturing member 34 spaced from the frangible cover 24, as seen in FIGS. 1, 2 and 3, to a closed position with the cover-rupturing member 34 extending through the frangible cover 24 and into the opening 16 of the fluid reservoir 14, as seen in FIGS. 4 and 5.

In the illustrated embodiments, the handle 12 has a cylindrical configuration which is hollow at least in the region of the fluid reservoir 14 adjacent to the base member 20, and can be hollow along the length of the handle between the base member 20 and an outer end 40 of the handle 12 to form the fluid reservoir 14 for permitting the handle to be filled with a fluid, such as an antiseptic solution. The base member 20 can be attached or integrally formed on the inner end 18 of the handle 12 and the base member 20 is oriented at an angle relative to the handle 12. In the illustrated configuration, as seen in FIG. 3, the base member 20 is oriented with the plane of its bottom surface 22 oriented at a 50 degree angle $\alpha$ relative to a longitudinal axis $A_L$ of the handle 12. It may be noted that the base member 20 may be formed as a plate-like planar member defined by the planar bottom surface 22 and having an opposing upper surface 42 extending laterally from the handle 12. Also, the base member 12 may have a circular configuration centered on the axis $A_L$ of the handle 12, as illustrated herein, or may comprise some other shape. However, the circular shape is preferred for providing a uniform distribution of fluid throughout the sponge-like member 30.

Referring to FIG. 1, the swab head 26 is formed with a through passage 43 that is aligned with the opening 16 of the fluid reservoir 14 when the swab head 26 is in the closed position. When the swab head 26 is pivoted to the closed position, the cover-rupturing member 34 can rupture the frangible cover 24 to permit fluid flow from the fluid reservoir 14 to the passage 43 and into the sponge-like member 30. The sponge-like member 30 can be formed of an open-cell foam that can permit controlled flow of fluid to an application side 45 of the sponge-like member 30. It should be understood that other materials may be provided for the sponge-like member 30 including sponges and fibrous materials.

In a preferred construction of the device 10, the device 10 may be formed of a molded construction and may be molded of, for example, polypropylene or ABS. Specifically, the handle 12, base member 20, swab head 26 and hinge segment 36 can form an integral unit 11, and are preferably formed integrally in a molding operation that simultaneously forms these elements. The hinge segment 36 can be formed as a living hinge integral with the base member 20 and with the swab head 26, and the living hinge may be defined at a crease or groove 44 extending along the pivot axis $A_P$, as seen in FIGS. 3 and 5. Accordingly, a flexible material is selected for molding the handle 12, base member 20, swab head 26 and hinge segment 36 in order to provide the required flexibility of the living hinge to maintain the base member 20 non-detachably connected to the swab head 26 throughout pivoting movement of the swab head 26 at the hinge segment 36.

The upper side 32 of the swab head 26 is formed as a planar surface which engages the bottom surface 22 of the base member 20 at a common plane $P_C$ (FIG. 4) when the swab head 26 is pivoted to a fully closed position. The planar surfaces of the base member 20 and swab head 26 are formed as flat sealing surfaces, both of which are positioned at the common plane $P_C$ to form a sealing interface that is intended to prevent leakage of fluid along the planar surfaces 22, 32 from the central location defined at the reservoir opening 16 to the peripheral edges 46, 48 of the base member 20 and swab head 26, respectively. It should be understood that within the context of describing sealing provided by the planar surfaces 22, 32, the frangible cover 24 is considered included with the planar surface 22 and can contact portions of the planar surface 32 in sealing engagement.

As a further barrier against leakage of fluid to the peripheral edges 46, 48 the swab head 26 can include a seal rib 50 (see FIGS. 1 and 5) extending from the planar surface defined by the upper side 32. The seal rib 50 engages the planar bottom surface 22 of the base member 20 when the swab head 26 is in the closed position to define a seal surrounding the opening 16 of the fluid reservoir 14 and the passage 43 in the swab head 26. Thus, the seal rib 50 provides a defined area beyond which fluid cannot pass in the event there is leakage between the planar sealing surfaces 22, 32. The seal rib 50 is preferably integrally molded on the upper side 32 of the swab head 26 and forms a thin line contact that can slightly deform the bottom surface 32 of the base member 20, as seen in FIG. 5. Alternatively, a seal rib may be formed in the bottom surface 22 of the base member 20 for engagement with the upper side 32 of the swab member 26.

Referring to FIGS. 1 and 5, a latch 51 extends upward from the swab head 26 for locking the swab head 26 in the closed position in engagement with the base member 20. The latch includes a latch tongue 52 that is integrally formed with the peripheral edge 48 of the swab head 26 on a diametrically opposite side of the swab head 26 from the hinge segment 36. The latch tongue 52 extends perpendicular to the upper side 32 of the swab head 26, and includes pawl means comprising a ridge 54 that extends from a distal edge of the latch tongue 52 and forms a recess 56 across the distal edge of the latch tongue 52 for receiving the peripheral edge 46 on the base member 20 in a snap lock engagement to retain the swab head 26 in the closed position. It may be noted that a width of the latch tongue 52 extends around a portion of the circumference of the peripheral edges 46, 48, wherein the circumferential extent of the latch tongue 52 is selected to create sufficient rigidity in the latch tongue 52 to permanently retain the swab head 25 in engagement with the base member 20. That is, the resistance to flexure of the latch tongue 52 can be decreased by increasing the width of the flexure tongue 52 in the circumferential direction of the peripheral edges 46, 48 to provide a positive snap lock retention of the swab head 26 in the closed position. It should be understood that in an alternative configuration, the latch tongue 51 could be provided mounted on the base member 20 for engagement of a distal end thereof with the peripheral edge 48 of the swab member 26.

Referring to FIGS. 1, 2, 5 and 6, the cover-rupturing member 34 is rigidly affixed to the upper side 32 of the swab head 26 at or adjacent to the through passage 43. For example, the cover-rupturing member 34 may be integrally molded with the swab head 26 extending upward from the upper side 32, and in the illustrated example is defined by semi-circular wall 60 having a base portion 61 (FIG. 5) located at the passage 43, surrounding a portion of the passage 43. An outer edge or outer surface 58 is defined by an edge of the wall 60 and includes opposing surface portions 58a, 58b (FIG. 6) extending from the upper side 32 and converging at an angle to an apex or point 62. Hence, it may be seen that the cover-rupturing member 34 is configured as a lancet for piercing the frangible cover 24. The cover-rupturing member 34 surrounding the through passage 43 in the swab head 26 forms a fluid conduit between the opening 16 of the fluid reservoir 14 and the sponge-like member 30.

The frangible cover 24 forms a seal over the opening 16 of the fluid reservoir 14 to seal in an antiseptic solution S (FIGS. 3 and 4). The frangible cover 24 is a thin membrane material and may be formed, for example, of aluminum foil or a plastic sheet. The device 10 may be supplied to a user, e.g., to medical personnel, with antiseptic solution S pre-packaged in the fluid reservoir 14 and with the swab head 26 retained in the open position, such as may be provided by packaging surrounding the device 10. In preparation for use, the device 10 is oriented by holding the handle 12 with the base member 20 located upward, and the swab head 26 is pivoted about the hinge segment 36 until the latch 51 locks in engagement over the peripheral edge 46 of the base member 20. During pivoting movement of the swab head 26, the cover rupturing member 34 engages and ruptures or pierces the frangible cover 24, placing an upper side 27 (FIG. 5) of the sponge-like member 30 in fluid communication with the fluid reservoir 14. The pivoted movement of the swab head 26 about the pivot axis $A_P$ provides a lever action that can provide increased piercing force for penetration of the cover-rupturing member 34 through the frangible cover 24. Orienting the handle 12 with the base member 20 positioned downward provides a flow of the antiseptic solution S from the fluid reservoir 14, passing through the cover-rupturing member 34 and the passage 43 into the sponge-like member 30 for use in applying the solution via the application side 45 to a treatment area on a patient.

Figure 7:
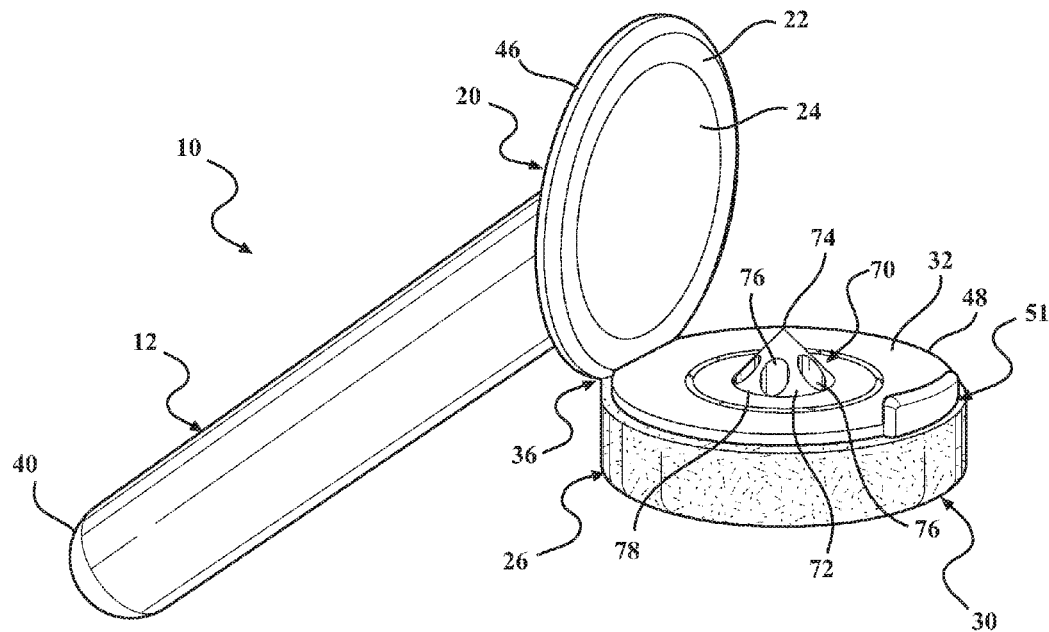
FIG. 7 is a perspective view illustrating the device in the open position with an alternative configuration for a closure-rupturing member.
Figure 8:
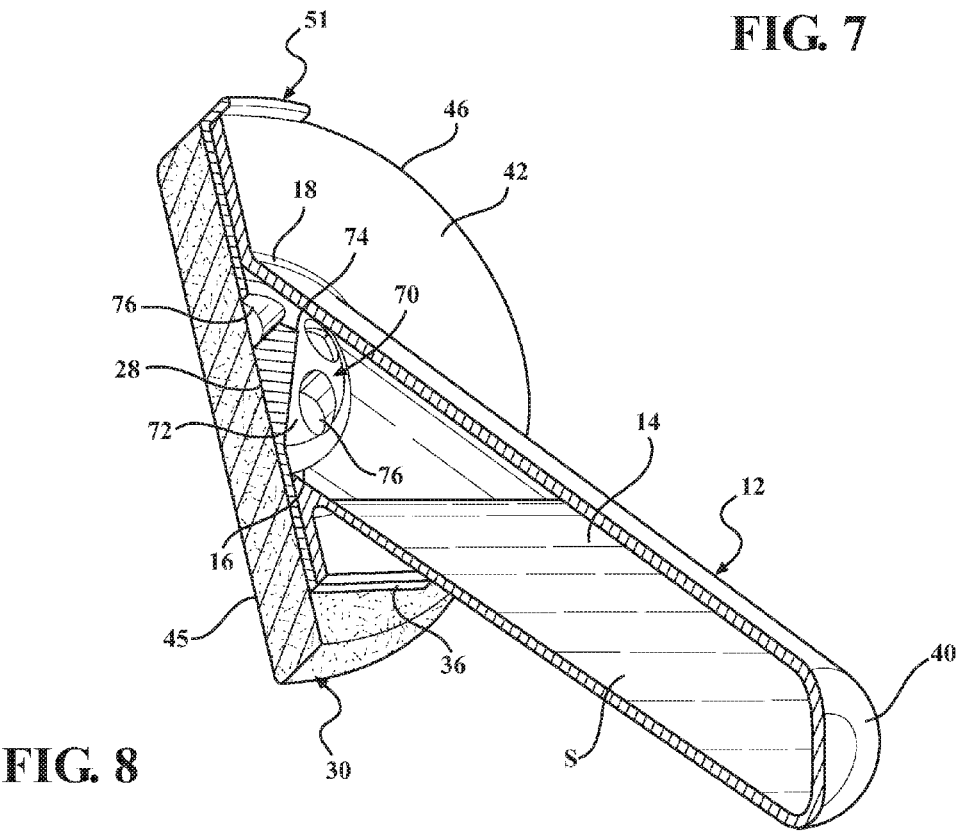
FIG. 8 is a perspective cross-sectional view illustrating the alternative configuration of FIG. 7 in the closed position.

Referring to FIGS. 7-8, an alternative configuration for a cover-rupturing member on the swab member 26 is illustrated, and is illustrated as a conical member 70 forming the cover-rupturing member. All other elements of the device 10 can be the same as for the device 10 described with reference to FIGS. 1-6, with the exception of the through passage which, in the present alternative configuration can comprise plural passages. The conical member 70 is rigidly affixed centrally on the upper side 32 of the swab member 26 and includes an outer surface 72. The outer surface 72 defines an angle with an apex 74 at a point located distal from the upper side 32 and extending to a peripheral base portion 78. A plurality of through passages 76 extend through the conical member 70 extending from the outer surface 72 to the lower side 28 of the swab member 26 within an area surrounded by the base portion 78 of the conical member 70. The fluid passages 76 define fluid conduits between the opening 16 of the fluid reservoir 14 and the sponge-like member 30.

The configuration of FIGS. 7-8 operates in a manner similar to that described for the configuration of FIGS. 1-6. As the swab member 26 is pivoted about the hinge segment 36, the conical member 70 can move into engagement with the frangible cover 24 to pierce the frangible cover 24. The swab member 26 is locked in engagement with the base member 20 by the latch 51 to define the closed position. Orienting the device 10 with the base member 20 positioned below the handle 12 provides a flow of the solution from the fluid reservoir 14, through the passages 76 of the conical member, into the sponge-like member 30.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid dispensing device comprising:
    an elongated member defining a handle having a hollow interior, the hollow interior defining a fluid reservoir having an opening at a lower end of the elongated member;
    a base member affixed to the lower end of the elongated member and having a bottom surface;

a frangible cover secured over the bottom surface and forming a seal across the opening of the fluid reservoir;

a swab head defining a lower side supporting an absorbent sponge-like member and an upper side supporting a cover-rupturing member; and a hinge segment affixed to the base member and to the swab head, the hinge segment defining a pivot axis about which the swab head pivots to move the swab head from an open position with the cover-rupturing member spaced from the frangible cover to a closed position with the cover-rupturing member extending through the frangible cover and into the opening of the fluid reservoir.

2. The device as set forth in claim 1, wherein the bottom surface of the base member and upper side of the swab head are planar surfaces and engage each other at a common plane in the closed position of the swab head.

3. The device as set forth in claim 2, one of the planar surfaces of base member and swab head includes a seal rib extending from the one of the planar surfaces, the seal rib engaging the other of the planar surfaces in the closed position to define a seal surrounding the opening of the fluid reservoir.

4. The device as set forth in claim 1, wherein the base member and swab head define respective peripheral edges and including a latch tongue integrally formed with the peripheral edge of one of the base member and the swab head, the latch tongue including pawl means forming a recess thereacross for engaging the peripheral edge on the other of the base member and the swab head to retain the swab head in the closed position.

5. The device as set forth in claim 1, wherein the hinge segment is a living hinge formed integrally with the base member and with the swab head.

6. The device as set forth in claim 1, including a through passage defined in the swab head aligned with the opening of the fluid reservoir in the closed position.

7. The device as set forth in claim 6, wherein the cover-rupturing member is rigidly affixed to the upper side at the through passage.

8. The device as set forth in claim 7, wherein the cover-rupturing member includes an outer surface defining an angle with an apex at a point located distal from the upper side.

9. The device as set forth in claim 8, wherein the cover-rupturing member includes a base portion surrounding the through passage in the swab head and the cover rupturing member defines a fluid conduit between the opening of the fluid reservoir and the sponge-like member.

10. The device as set forth in claim 1, where the frangible cover comprises a thin sheet of material adhered to the bottom surface of the base member.

11. A liquid dispensing device comprising:

an elongated member defining a handle having a hollow interior, the hollow interior defining a fluid reservoir having an opening at a lower end of the elongated member;

a base member affixed to the lower end of the elongated member and having a bottom surface;

a frangible cover comprising a thin sheet of material adhered to the bottom surface of the base member and forming a seal across the opening of the fluid reservoir;

a swab head comprising a plate-like member defining a lower side supporting an absorbent sponge-like member and an upper side with a cover-rupturing member comprising an upward projection rigidly affixed to the upper side, the swab head including a through passage for passage of fluid from the fluid reservoir to the sponge-like member; and a hinge segment affixed to the base member and to the swab head, the hinge segment defining a pivot axis about which the swab head pivots to move the swab head from an open position with the cover-rupturing member spaced from the frangible cover to a closed position with the cover-rupturing member extending through the frangible cover and into the opening of the fluid reservoir.

12. The device as set forth in claim 11, wherein the bottom surface of the base member and upper side of the swab head are planar surfaces and engage each other at a common plane in the closed position of the swab head.

13. The device as set forth in claim 12, one of the planar surfaces of base member and swab head includes a seal rib extending from the one of the planar surfaces, the seal rib engaging the other of the planar surfaces in the closed position to define a seal surrounding the opening of the fluid reservoir.

14. The device as set forth in claim 11, wherein the base member and swab head define respective peripheral edges and the hinge segment is a living hinge formed integrally with the peripheral edges of the base member and the swab head.

15. The device as set forth in claim 14, including a latch tongue integrally formed with the peripheral edge of one of the base member and the swab head, opposite from the hinge segment, the latch tongue including pawl means forming a recess thereacross for engaging the peripheral edge on the other of the base member and the swab head to retain the swab head in the closed position.

16. The device as set forth in claim 11, wherein the cover-rupturing member includes an outer surface defining an angle with an apex at a point located distal from the upper side.

17. The device as set forth in claim 16, wherein the cover-rupturing member includes a base portion surrounding the through passage in the swab head and the cover-rupturing member defines a fluid conduit between the opening of the fluid reservoir and the sponge-like member.

18. A liquid dispensing device comprising:

an elongated member defining a handle having a hollow interior, the hollow interior defining a fluid reservoir having an opening at a lower end of the elongated member;

a base member affixed to the lower end of the elongated member and having a planar bottom surface, and a peripheral edge defined around the base member;

a frangible cover comprising a thin sheet of material adhered to the bottom surface of the base member and forming a seal across the opening of the fluid reservoir retaining a fluid within the fluid reservoir;

a swab head comprising a plate-like member defining a lower side supporting an absorbent sponge-like member and an upper side with a cover-rupturing member comprising an upward projection rigidly affixed to the upper side, the swab head defining a peripheral edge and including a through passage for passage of fluid from the fluid reservoir to the sponge-like member;

a living hinge formed integrally with the base member and with the swab head, the hinge defining a pivot axis about which the swab head pivots to move the swab head from an open position with the cover-rupturing member spaced from the frangible cover to a closed position with the cover-rupturing member extending through the frangible cover and into the opening of the fluid reservoir; and a latch tongue integrally formed with the peripheral edge of one of the base member and the swab head, the latch tongue including pawl means forming a recess thereacross for engaging the peripheral edge on the other of the base member and the swab head to retain the swab head in the closed position.

* * * * *